(12) United States Patent
Tomblyn et al.

(10) Patent No.: US 9,827,245 B2
(45) Date of Patent: Nov. 28, 2017

(54) KERATIN COMPOSITIONS COMPRISING HALOFUGINONE

(71) Applicant: KeraNetics, LLC, Winston-Salem, NC (US)

(72) Inventors: Seth Tomblyn, Belmont, NC (US); Luke Burnett, Winston-Salem, NC (US); Scott Washburn, Pfafftown, NC (US)

(73) Assignee: KeraNetics, LLC, Winston-Salem, NC (US)

( * ) Notice: Subject to any disclaimer, the term of this patent is extended or adjusted under 35 U.S.C. 154(b) by 0 days.

(21) Appl. No.: 14/215,601

(22) Filed: Mar. 17, 2014

(65) Prior Publication Data
US 2015/0025015 A1 Jan. 22, 2015

Related U.S. Application Data

(60) Provisional application No. 61/788,971, filed on Mar. 15, 2013.

(51) Int. Cl.
*A61K 38/00* (2006.01)
*A61K 31/517* (2006.01)
*A61K 38/17* (2006.01)
*A61K 9/19* (2006.01)

(52) U.S. Cl.
CPC .............. *A61K 31/517* (2013.01); *A61K 9/19* (2013.01); *A61K 38/1748* (2013.01)

(58) Field of Classification Search
None
See application file for complete search history.

(56) References Cited

U.S. PATENT DOCUMENTS

| | | | |
|---|---|---|---|
| 4,570,629 A * | 2/1986 | Widra | 604/304 |
| 5,006,467 A | 4/1991 | Kusano et al. | |
| 5,047,249 A | 9/1991 | Rothman et al. | |
| 5,100,783 A | 3/1992 | Dean, Jr. et al. | |
| 5,153,132 A | 10/1992 | Goodwin et al. | |
| 5,300,285 A | 4/1994 | Halloran et al. | |
| 5,320,796 A | 6/1994 | Harashima et al. | |
| 5,358,935 A | 10/1994 | Smith et al. | |
| 5,512,474 A | 4/1996 | Clapper et al. | |
| 5,634,945 A | 6/1997 | Pernia et al. | |
| 5,636,643 A | 6/1997 | Argenta et al. | |
| 5,645,081 A | 7/1997 | Argenta et al. | |
| 5,651,966 A | 7/1997 | Read et al. | |
| 5,679,819 A | 10/1997 | Jones et al. | |
| 5,707,972 A | 1/1998 | Shimizu | |
| 5,763,583 A | 6/1998 | Arai et al. | |
| 5,852,024 A * | 12/1998 | Pines et al. | 514/266.22 |
| 5,883,078 A | 3/1999 | Seelich et al. | |
| 5,902,608 A | 5/1999 | Read et al. | |
| 5,932,552 A * | 8/1999 | Blanchard et al. | 424/445 |
| 5,948,432 A | 9/1999 | Timmons et al. | |
| 5,972,335 A | 10/1999 | Ferguson et al. | |
| 6,110,487 A | 8/2000 | Timmons et al. | |
| 6,124,265 A | 9/2000 | Timmons et al. | |
| 6,159,495 A | 12/2000 | Timmons et al. | |
| 6,159,496 A | 12/2000 | Blanchard et al. | |
| 6,165,496 A | 12/2000 | Timmons et al. | |
| 6,268,454 B1 | 7/2001 | Song et al. | |
| 6,270,791 B1 | 8/2001 | Van Dyke et al. | |
| 6,270,793 B1 | 8/2001 | Van Dyke et al. | |
| 6,274,155 B1 | 8/2001 | Van Dyke et al. | |
| 6,274,163 B1 | 8/2001 | Blanchard et al. | |
| 6,316,598 B1 | 11/2001 | Van Dyke et al. | |
| 6,371,984 B1 | 4/2002 | Van Dyke et al. | |
| 6,379,690 B2 | 4/2002 | Blanchard et al. | |
| 6,432,435 B1 | 8/2002 | Timmons et al. | |
| 6,461,628 B1 | 10/2002 | Blanchard et al. | |
| 6,544,548 B1 | 4/2003 | Siller-Jackson et al. | |
| 6,696,073 B2 | 2/2004 | Boyce et al. | |
| 6,746,836 B1 | 6/2004 | Widra | |
| 6,783,546 B2 | 8/2004 | Zucherman et al. | |
| 6,808,927 B2 | 10/2004 | Greenfield et al. | |
| 6,825,323 B2 | 11/2004 | Hess | |
| 6,833,488 B2 | 12/2004 | Bucevschi et al. | |
| 6,858,383 B2 | 2/2005 | Sabbadini | |
| 6,869,445 B1 | 3/2005 | Johnson | |
| 7,148,327 B2 | 12/2006 | Kelly et al. | |
| 7,439,012 B2 | 10/2008 | Van Dyke | |
| 7,892,572 B2 | 2/2011 | Peplow et al. | |
| 7,892,573 B2 | 2/2011 | Van Dyke | |
| 8,021,830 B2 | 9/2011 | Van Dyke | |
| 8,258,093 B2 | 9/2012 | Van Dyke | |
| 8,273,702 B2 | 9/2012 | Van Dyke | |
| 8,299,013 B2 | 10/2012 | Van Dyke | |
| 2001/0021389 A1 | 9/2001 | Starling et al. | |
| 2001/0047082 A1 | 11/2001 | Van Dyke et al. | |
| 2002/0192196 A1 | 12/2002 | Allen-Hoffmann | |
| 2003/0049266 A1 | 3/2003 | Fearon et al. | |
| 2003/0109587 A1 | 6/2003 | Mori | |
| 2003/0228353 A1 | 12/2003 | Cowsar | |

(Continued)

FOREIGN PATENT DOCUMENTS

| | | |
|---|---|---|
| WO | WO 99/26570 | 6/1999 |
| WO | WO 99/26595 | 6/1999 |
| WO | WO 99/51175 | 10/1999 |
| WO | WO 00/76437 | 12/2000 |
| WO | WO 01/19283 | 3/2001 |
| WO | WO 01/19305 | 3/2001 |
| WO | WO 01/64033 | 9/2001 |
| WO | WO 02/45508 | 6/2002 |
| WO | WO 03/011894 | 2/2003 |
| WO | WO 03/064449 | 8/2003 |

(Continued)

OTHER PUBLICATIONS

Peyton et. al. journal of surgical research 178 (2012) 545-552.*
Peyton, Charles C., "Halofuginone infused keratin hydrogel attenuates adhesions in a rodent cecal abraision model", Journal of Surgical Research, Wake Forest Univ. School of Medicine, Winston Salem, NC, 2012.

*Primary Examiner* — Jeanette Lieb
(74) *Attorney, Agent, or Firm* — Mintz Levin Cohn Ferris Glovsky and Popeo, P.C.

(57) ABSTRACT

Described herein are compositions of keratin-based biomaterials together with halofuginone and methods of using thereof.

16 Claims, 5 Drawing Sheets

(56) References Cited

U.S. PATENT DOCUMENTS

Figure 1A:
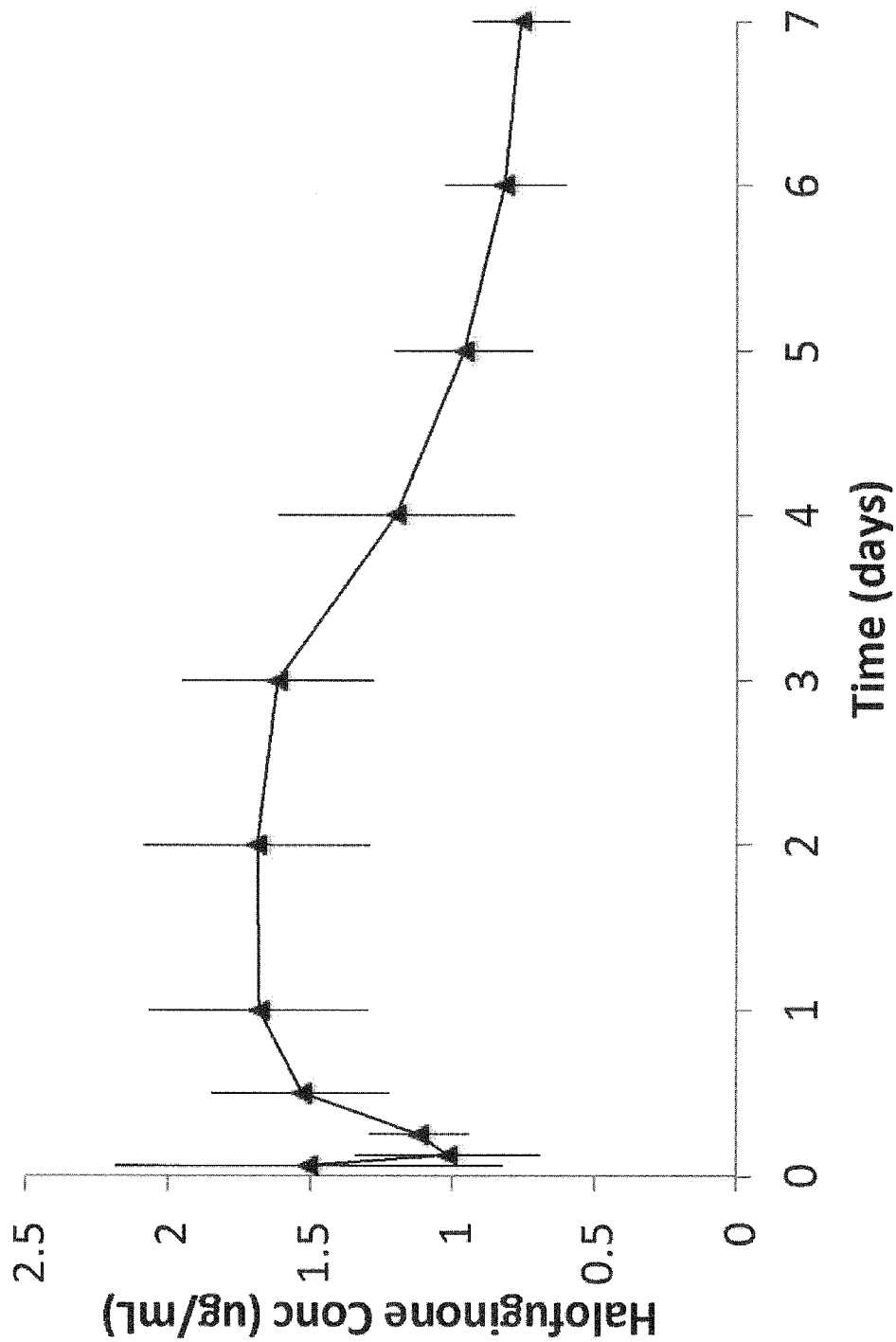

| | | |
|---|---|---|
| 2004/0062793 A1 | 4/2004 | Van Dyke |
| 2004/0076599 A1 | 4/2004 | Siller-Jackson et al. |
| 2004/0078090 A1 | 4/2004 | Binette et al. |
| 2004/0120910 A1 | 6/2004 | Van Dyke |
| 2004/0267362 A1 | 12/2004 | Hwang et al. |
| 2005/0058686 A1 | 3/2005 | Van Dyke |
| 2005/0084542 A1 | 4/2005 | Rosenberg et al. |
| 2006/0051732 A1 | 3/2006 | Van Dyke |
| 2007/0166348 A1 | 7/2007 | Van Dyke |
| 2007/0208134 A1* | 9/2007 | Hunter et al. ............... 525/54.1 |
| 2007/0298070 A1 | 12/2007 | Van Dyke |
| 2008/0003676 A1 | 1/2008 | Sheridan et al. |
| 2008/0038327 A1 | 2/2008 | Kelly et al. |
| 2008/0274165 A1 | 11/2008 | Van Dyke |
| 2009/0004242 A1 | 1/2009 | Van Dyke |
| 2009/0017001 A1 | 1/2009 | Van Dyke |
| 2009/0017031 A1 | 1/2009 | Fung |
| 2009/0047260 A1 | 2/2009 | Van Dyke |
| 2010/0197021 A1 | 8/2010 | Van Dyke |
| 2011/0137329 A1 | 6/2011 | Van Dyke |
| 2011/0217285 A1* | 9/2011 | Van Dyke ............ A61K 9/0019 424/94.64 |
| 2011/0300193 A1 | 12/2011 | Van Dyke |

FOREIGN PATENT DOCUMENTS

| | | |
|---|---|---|
| WO | WO 03/086491 | 10/2003 |
| WO | WO 2004/011052 | 2/2004 |
| WO | WO 2007/001339 | 1/2007 |
| WO | WO 2007/050387 | 3/2007 |
| WO | WO 2007/050387 | 5/2007 |
| WO | WO 2007/095151 | 8/2007 |
| WO | WO 2007/098053 | 8/2007 |
| WO | WO 2007/098114 | 8/2007 |
| WO | WO 2008/070091 | 6/2008 |
| WO | WO 2008/130607 | 10/2008 |

* cited by examiner

KERATIN COMPOSITIONS COMPRISING HALOFUGINONE

This application is non-provisional application which claims benefit of U.S. Provisional Patent Application Ser. No. 61/788,971, filed Mar. 15, 2013, the contents of which are hereby incorporated herein in their entirety by reference.

1. FIELD

Described herein are compositions of keratin protein-based biomaterials comprising halofuginone and methods of using such compositions.

2. BACKGROUND

Keratins are a family of proteins found in the hair, skin, and other tissues of vertebrates. Hair is a unique source of human keratins because it is one of the few human tissues that are readily available and inexpensive.

Keratins can be extracted from human hair fibers by oxidation or reduction using methods that have been widely published in the art. If one employs a reductive treatment, the resulting keratins are referred to as kerateines. If an oxidative treatment is used, the resulting keratins are referred to as keratoses. These methods typically employ a two-step process whereby the crosslinked structure of keratins is broken down by either oxidation or reduction. In these reactions, the disulfide bonds in cystine amino acid residues are cleaved, rendering the keratins soluble without appreciable disruption of amide bonds. Many of the keratins can remain trapped within the cuticle's protective structure, so a second-step using a denaturing solution is typically employed to effect efficient extraction of the cortical proteins (alternatively, in the case of oxidation reactions, these steps can be combined). This step has also been widely published in the art as solutions such as urea, transition metal hydroxides, surfactant solutions, and combinations thereof have been employed. Common methods employ the use of aqueous solutions of tris(hydroxymethyl) aminomethane in concentrations between 0.1 and 1.0M, and urea solutions between 0.1 and 10M.

When oxidation is selected as the extraction method of choice, strong oxidants are used to cleave the cystine amino acid and solubilize the keratin proteins. A preferred oxidant is peracetic acid. Peracetic acid ($CH_3COOOH$) hydrolyzes into acetic acid ($CH_3COOH$) and hydrogen peroxide ($H_2O_2$). It also undergoes homolysis to produce peroxyl ($CH_3COO^-$; $CH_3COOO^-$), hydrogen ($H^+$), and hydroxyl (HO) radicals. Hydroxyl radicals are very strong oxidizing agents due to their high standard reduction potential (2310 mV). When reacted with $HO^-$, proteins decompose into fragments with carbonyl groups (—C=O) in the presence of oxygen ($O_2$) and a small fraction forms protein aggregates via cross-linking. Both of these degraded and cross-linked forms are observed in keratose samples. Aside from oxidation of cystine, peracetic acid (most likely through the action of $HO^-$ and $H_2O_2$)) also reacts and modifies other amino acids of the protein chain. The free thiols (—SH) of cysteines are converted to sulfenic acid (—SOH), which are further oxidized into sulfinic (—$SO_2H$) and sulfonic acid derivatives.

The ability to form a polymerized hydrogel is an important feature in biomaterials used as scaffolds for cells, agents for drug delivery or constructs to promote cell infiltration and tissue remodeling. Hydration of lyophilized keratose materials generally yields the formation of an elastic solid-like hydrogel at high solute concentrations (200 mg/ml in PBS). Rheological properties of these gels as well as their chemistries indicate that the primary mechanism of gelation is through polymer chain entanglement. Oxidation of free thiols eliminates the ability of oxidized keratins to reassemble via covalent disulfide bonding. Instead, other gelation determinant factors may include electrostatic and hydrophobic interaction. Keratin multimers may form a larger network through electrostatic attraction as suggested in the assembly of intermediate filament molecules in which the head (positive) and the tail (negative) domains of dimers potentially associate to form a tetramer. The negatively-charged sulfonic acid groups can also interact with the basic amino acid residues such as lysine, arginine, and histidine that escaped oxidation. Additionally, the coil regions of keratins that are rich in hydrophobic sequences may aggregate together to increase the polymer molecular weight and promote gelation.

Current Burn and Scar Treatment

Currently, the most effective treatments to manage burn-related scarring and contracture remain elusive and controversial. There is a broad agreement that contracture is far less likely if hypertrophic scars are prevented. Current treatments designed to prevent hypertrophic scar formation include silicone sheets or gels over the burn for weeks post injury, occlusive dressings, pressure garment therapy, silver sulfadiazine corticosteroids, and treating existing scars with laser ablation or excision. None of these treatments show particular effectiveness in preventing burn scarring with associated primary or secondary contracture. Accordingly, there is an unmet need of providing a highly efficient burn wound treatment.

Proud Flesh and Horses

Wounds on the legs of a horse, especially near a joint where there is motion, have tissue that is fairly fragile and very tight. The new tissue continues to rebuild itself causing excessive or exuberant granulation tissue. This phenomenon is also known as proud flesh. Until recently there has been no cure for proud flesh. There are many topical powders and solutions that typically remove the granulation tissue, but also remove surrounding healthy tissue as well, while causing pain to the treated horse when the healthy tissue is impacted. Home remedies such as creating a paste of sugar and iodine as a cover up, and some suggest using meat tenderizer. None of these ideas work. Oftentimes the only solution has been for the veterinarian to physically cut away or cauterize the excessive tissue and wrap the wound tightly trying to immobilize the wound and hope that the proud flesh does not grow back.

Halofuginone

Halofuginone is a coccidiostat used in veterinary medicine. It is a synthetic halogenated derivative of febrifugine, a natural quinazolinone alkaloid which can be found in the Chinese herb *Dichroa febrifuga*.

Halofuginone inhibits the development of T helper 17 cells, immune cells that play an important role in autoimmune disease, but it does not affect other kinds of T cells which involved in normal immune function. The drug is a potent, non-toxic inhibitor of type-1 collagen synthesis. Halofuginone both prevents TGF-beta induction of type-1 collagen synthase, but also phosphorylation of smad3. Type I collagen is the principal constituent of scar tissue, including Proud Flesh.

Using Proud Flesh wounds as a model for burn wound recovery, the inventors sought to develop topical compositions with halofuginone that, when applied to the wound, would improve the efficiency and completeness of recovery and decrease the need for surgery.

3. SUMMARY

Disclosed herein are compositions of keratin-based biomaterials together with halofuginone and methods of using thereof.

4. BRIEF DESCRIPTION OF THE FIGURES

Figure 1B:
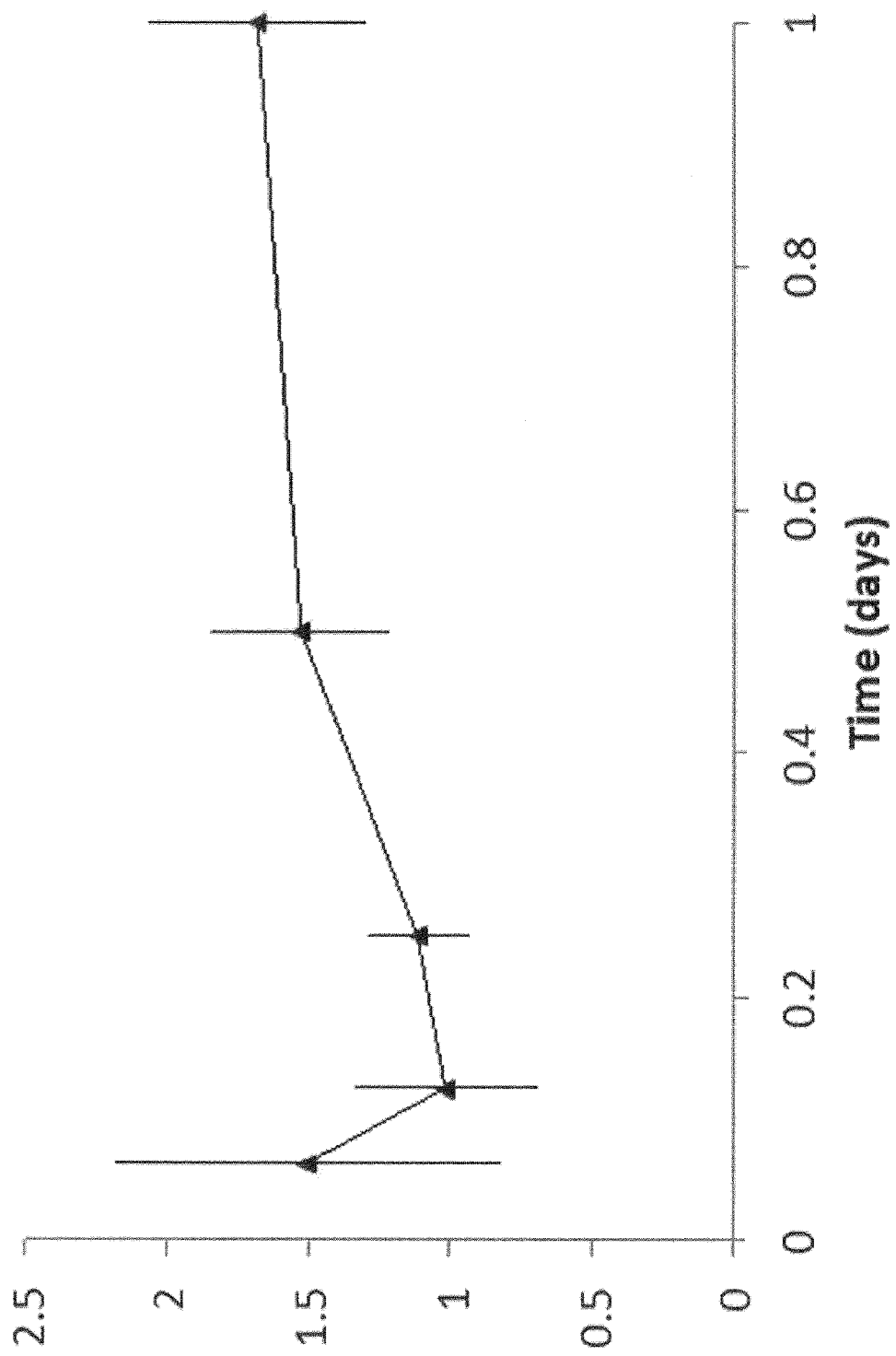
Figure 1C:
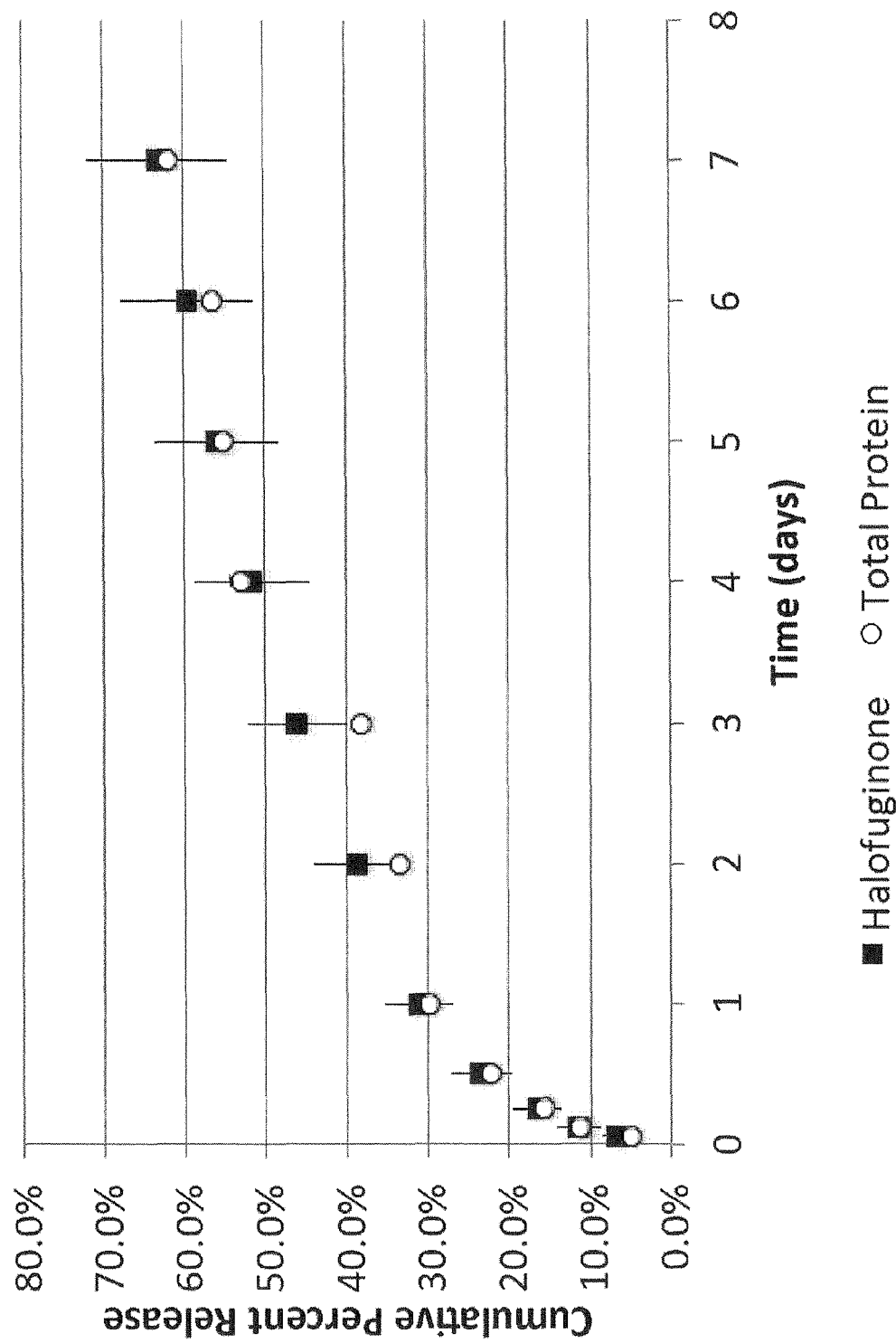

FIGS. 1A-C depict the characteristics of release of halofuginone from keratin based hydrogels. FIG. 1A depicts the release of halofuginone from keratin based hydrogels over time. Halofuginone was present within the hydrogel at a concentration of 22 µg/mL. The release of the halofuginone into PBS buffer was measured over several days. The buffer concentration of 1.5 µg/mL of drug was constant over days 1-4 and slowly decreased thereafter. FIG. 1B shows the release characteristics in the first 24 hours. FIG. 1C depicts halofuginone release and keratin protein release from the hydrogel expressed as a percentage of the original amount of drug/protein present within the hydrogel. Correlation between the halofuginone release and keratin protein release (degradation) is greater that 0.98, n=3 for each data point with SEM.

Figure 2:
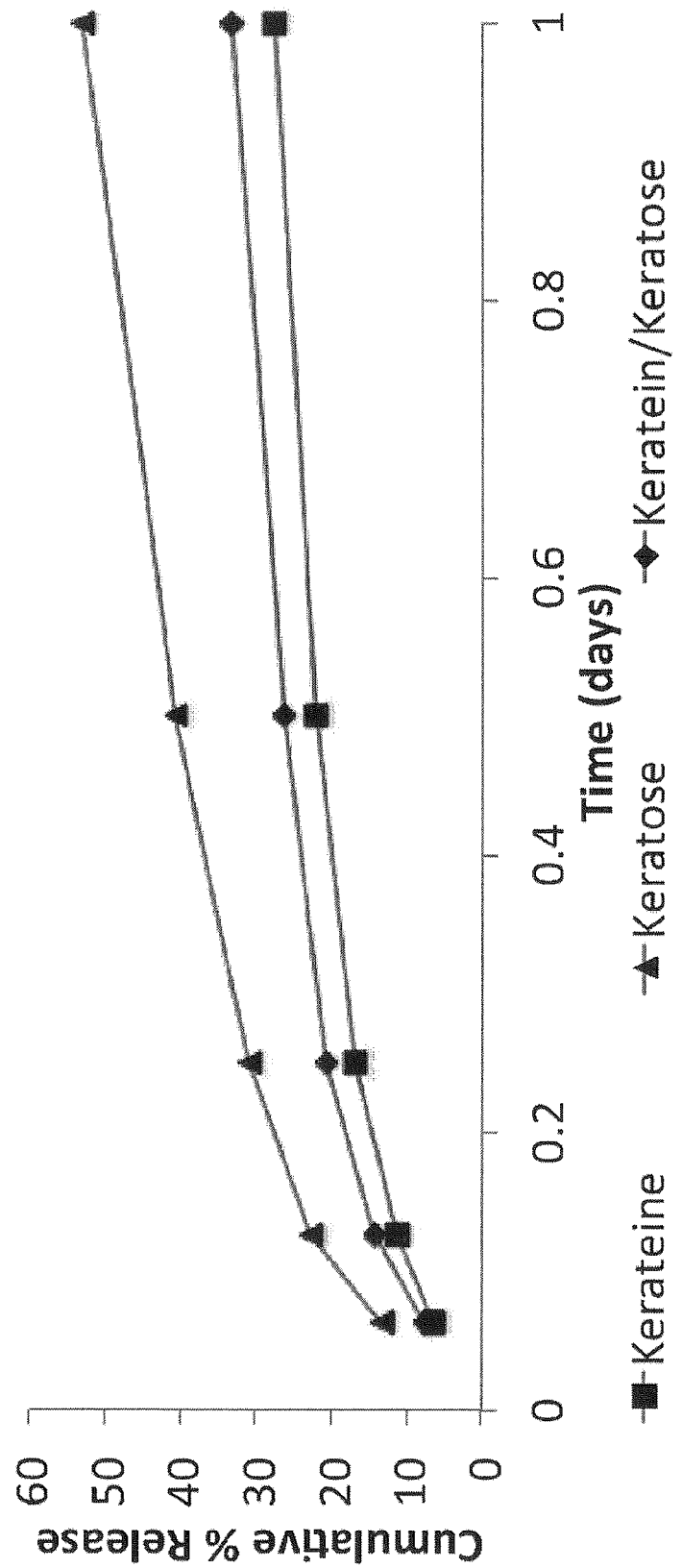

FIG. 2 depicts the release of halofuginone from Kerateine, Keratose and mixtures of Kerateine and Keratose hydrogel formulations expresses as a percentage of the original amount of drug present within the hydrogel.

Figure 3:
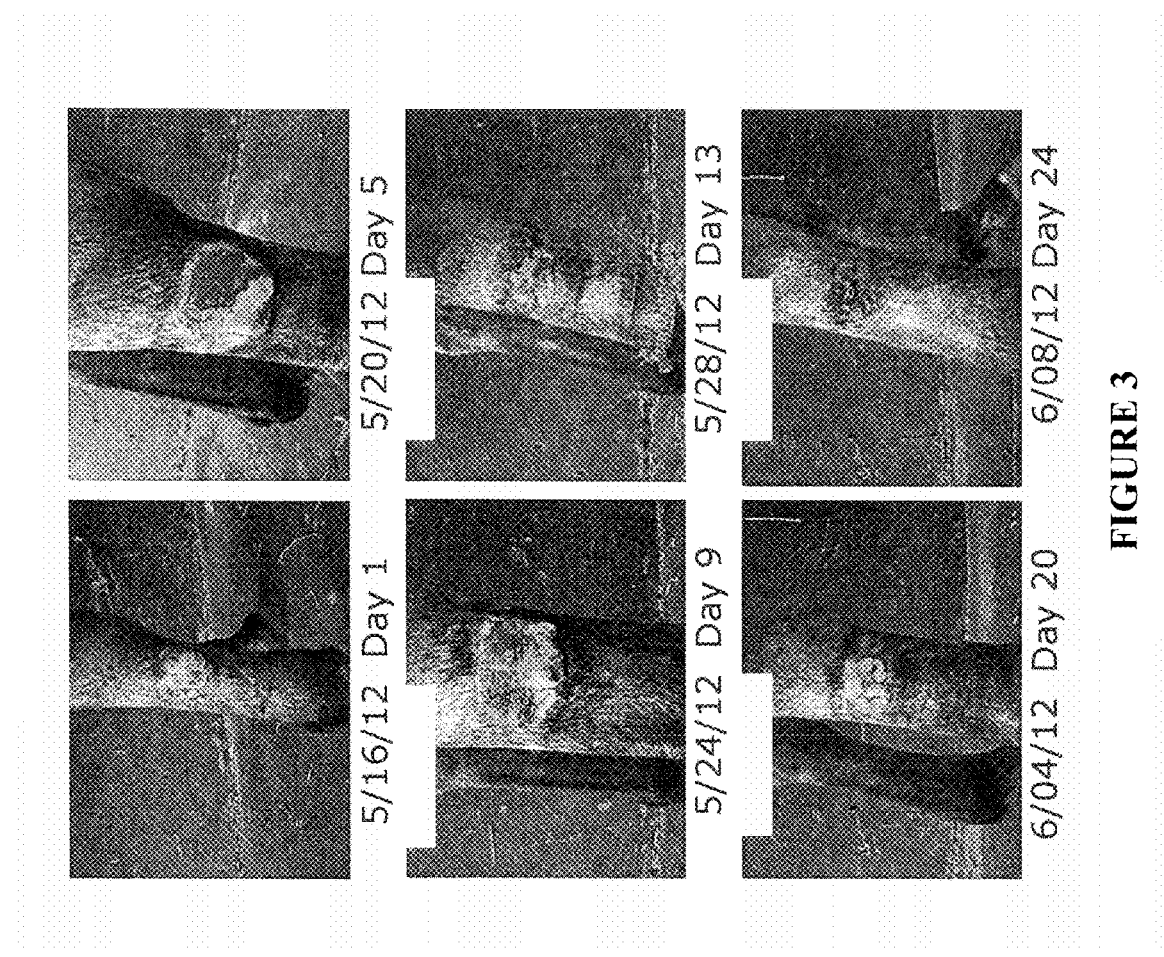

FIG. 3 depicts halofuginone containing keratin based hydrogels used to treat a hypergranulation wound in an equine subject. Shown in FIG. 3 are images of wounds on one horse receiving treatment with an halofuginone containing keratin based hydrogel. The scab debrided every other day and the hydrogel was applied to prevent hypergranulation reoccurrence. By day 18-24, the wound is nearly healed.

5. DETAILED DESCRIPTION

"Keratin protein source" as used herein includes proteinaceous sources of keratin proteins including but not limited to human or animal hair, wool, fur, horns, hooves, beaks, feathers, scales, and the like.

"Keratin protein(s)" as used herein collectively refers to keratin in keratin protein sources, including but not limited to naturally occurring keratin, reduced keratin, and/or oxidized keratin, or S-sulfonated keratin. This term also refers to the extracted keratin derivatives that are produced by oxidative and/or reductive treatment of keratin, including but not limited to keratose, alpha-keratose, gamma-keratose, kerateine, alpha-kerateine, or gamma-kerateine.

Keratin Protein Sources

Keratins are a family of proteins found in the hair, skin, and other tissues of vertebrates. Hair is a common source of human keratins because it is one of the few human tissues that are readily available and inexpensive. Other sources of keratins are acceptable feedstocks for the present invention, (e.g., wool, fur, horns, hooves, beaks, feathers, scales, and the like). Human hair is often used with human subjects because of its biocompatibility. Accordingly, in some embodiments, human hair is the keratin protein source. The human hair can be end-cut, as one would typically find in a barber shop or salon.

Keratin Proteins

Soluble keratins can be extracted from human hair fibers by oxidation or reduction using methods known in the art. These methods typically employ a two-step process whereby the crosslinked structure of keratins is broken down by either oxidation or reduction. In these reactions, the disulfide bonds in cystine amino acid residues are cleaved, rendering the keratins soluble. The cuticle is essentially unaffected by this treatment, so the majority of the keratins remain trapped within the cuticle's protective structure. In order to extract these keratins, a second step using a denaturing solution is employed. Alternatively, in the case of reduction reactions, these steps can be combined. Denaturing solutions known in the art include urea, transition metal hydroxides, surfactant solutions, and combinations thereof. Common methods use aqueous solutions of tris base (2-Amino-2-(hydroxymethyl)-1,3-propanediol) in concentrations between 0.1 and 1.0 M, and urea solutions between 0.1 and 10M, for oxidation and reduction reactions, respectively.

If one employs an oxidative treatment, the resulting keratins are referred to as "keratoses." If a reductive treatment is used, the resulting keratins are referred to as "kerateines."

Crude (unfractionated) extracts of keratins, regardless of redox state, can be further refined into matrix (KAP and gamma), alpha, and/or charged (acidic or basic) fractions by a variety of methods such as isoelectric precipitation, dialysis, or high performance liquid chromatography (HPLC), as desired. In a crude extract, the alpha fraction begins to precipitate below pH 6 and is essentially completely precipitated by pH 4.2.

In some embodiments, KAP co-precipitate with the alpha fraction, thereby producing an alpha/KAP mixture.

High molecular weight keratins, or "alpha keratins," (alpha helical), are thought to originate from the microfibrillar regions of the hair follicle, and typically range in molecular weight from about 40-85 kiloDaltons. Low molecular weight keratins, or "gamma keratins," or keratin-associated proteins (KAPs, globular), are thought to originate from the matrix regions of the hair follicle, and typically range in molecular weight from about 3-30 kiloDaltons for KAP and 10-15 kiloDaltons for gamma keratins In some embodiments, the keratin preparations (particularly alpha-keratose or alpha-kerateine) have average monomeric molecular weights of from about 45 to about 70 kiloDaltons. Gamma-keratoses and Gamma-kerateines have average molecular weights between 10 and 25 kiloDaltons and form complexes with alpha keratins. The alpha keratins extracted and described herein exist as obligate heterodimers that are complexed alpha keratin monomers with higher average molecular weights, e.g., up to 100 or 200 or 300 or 400 or 500 kiloDaltons. These combinations when complexed (e.g. alpha keratose, gamma keratose, alpha kerateine, gamma kerateine or combinations thereof) are termed "metakeratins".

Even though alpha and gamma keratins possess unique properties, the properties of subfamilies of both alpha and gamma keratins can only be revealed through more sophisticated means of purification and separation such as provided herein. Additional properties that are beneficial emerge and can be optimized upon further separation and purification of crude keratin extracts.

Keratose Production

One method for the production of keratoses is by oxidation of keratin with hydrogen peroxide, peracetic acid, or performic acid. In a specific embodiment, the oxidant is peracetic acid. Generally, a solution of peracetic acid is used at a concentration range of about 1% to about 10%. A specific concentration used can be a 2% solution of peracetic acid. In some embodiments, the oxidant concentrations range from a ratio of about 5:1 to about 50:1 weight to weight to the keratin protein source to be extracted. A specific embodiment uses a weight to weight ratio of 25:1 of a 2% peracetic acid solution. Those skilled in the art will recognize that slight modifications to the concentration can be made to affect varying degrees of oxidation, with concomitant alterations in reaction time, temperature, and liquid to solid ratio. It has also been discussed by Crewther et al. that performic acid offers the advantage of minimal peptide bond cleavage compared to peracetic acid. However, peracetic acid offers the advantages of cost and availability. In some embodiments, the oxidation temperature is between 0 and 100° Celsius. In a specific embodiment, the oxidation temperature is 37° C. In some embodiments, the oxidation time is between 0.5 and 24 hours. In a specific embodiment, the oxidation time is 12 hours. In some embodiments, mechanical mixing is used to maximize oxidation efficiency. Additional yield can be achieved with subsequent extractions with dilute solutions of oxidant, or water. After oxidation, the keratin protein source can be rinsed free of residual oxidant using purified water. In some embodiments, the oxidized keratin protein source is washed with water until residual oxidant is removed. In some embodiments, the washing step is performed until the washed keratin protein source does not test positive for oxidant.

The keratoses may be extracted from the oxidized keratin protein source using an aqueous solution of a denaturing agent. Protein denaturants are well known in the art, including but not limited to, urea, transition metal hydroxides (e.g. sodium and potassium hydroxide), ammonium hydroxide, and tris(hydroxymethyl)aminomethane (Tris, also known as Trizma® base). In some embodiments, Tris is used at a ratio of about 5:1 to about 50:1 weight of protein source, to a Tris solution of a concentration of about 0.01 to 1M. In a specific embodiment, the ratio is 25:1. In another specific embodiment, Tris is used at a concentration of 100 mM. Those skilled in the art will recognize that slight modifications to the concentration can be made to effect varying degrees of extraction, with concomitant alterations in reaction time, temperature, and liquid to solid ratio. In some embodiments, the extraction temperature is between 0° and 100° C. In a specific embodiment, the extraction temperature is 37° C. In some embodiments, the extraction time is between 0.5 and 24 hours. In a specific embodiment, the extraction time is about 2 hours. Additional yield can be achieved with subsequent extractions with dilute solutions of Tris or purified water. Often, the extraction is performed with mechanical agitation in a mixing tank to ensure a more efficient yield.

Kerateine Production

Similar to the methods described above for extraction and purification of keratoses, kerateines can be produced by reduction of a keratin protein source with thioglycolic acid or beta-mercaptoethanol. Specifically, thioglycolic acid (TGA) is often used. In some embodiments, TGA is added to the keratin protein source at a ratio of about 5:1 to about 50:1. In a specific embodiment, TGA is added at a ratio of 25:1. The TGA is added at a solution ranging in concentrations from about 0.1 to about 10M. In a specific embodiment, the TGA is added in solution at a concentration of 0.5M. During extraction, mechanical agitation is used to maximize extraction efficiency.

The solution containing reductant and extracted kerateine proteins (soluble keratin protein solution) is the collected and stored by straining the keratin protein source through a 400 micron mesh and storing the solution at 4° C. A base is then added to the drained keratin protein source in a ratio of about 10:1 to about 50:1. In a specific embodiment, the base is added to the drained keratin protein source at a ratio of 25:1. In some embodiments, the base is Tris generally used at a concentration of about 100 mM. The keratin protein source in the solution with base is mixed with agitation for about 2 hours at 37° C. The solution containing the base and extracted keratin proteins (soluble keratin protein solution) is then filtered through a added to the first extracted solution and stored Those skilled in the art will recognize that slight modifications to the concentration can be made to effect varying degree of reduction, with concomitant alterations in pH, reaction time, temperature, and liquid to solid ratio. In some embodiments, the reduction is performed at a temperature between 0 and 100° C. In a specific embodiment, the temperature is 37° C. In some embodiments, the reduction time is between 0.5 and 24 hours. In a specific embodiment, the reduction is performed for 15 hours. Unlike the previously described oxidation reaction, reduction is carried out at basic pH. Keratins are highly soluble in a reduction media and are expected to be extracted. The reduction solution may therefore be combined with the subsequent extraction solutions and processed accordingly. The reduction is carried out with mechanical agitation in a mixing tank to increase the efficiency of the reduction of the keratin proteins.

Residual reductant and denaturing agents can be removed from solution by dialysis. Typical dialysis conditions are 1 to 2% solution of kerateines dialyzed against purified water. Those skilled in the art will recognize that other methods exist for the removal of low molecular weight contaminants in addition to dialysis (e.g. microfiltration, chromatography, and the like). Once dissolved, the kerateines are stable in solution without the denaturing agent for finite periods. Therefore, the denaturing agent can be removed without the resultant precipitation of kerateines. Regardless of the fractionation/purification process, the resulting kerateines can be concentrated and lyophilized, similar to keratoses.

A soluble keratin protein solution is produced by the extraction of keratose and/or kerateine by either oxidative means for keratose, or by reductive means for kerateine.

High Speed Centrifugation

In order to remove many of the keratin associated proteins and other proteins extracted through either oxidative or reductive processes listed above, a high speed centrifugation step is used. Current methods known in the art generally use a low speed centrifugation (around 4,000 rpm) to clear particulate matter. However, this speed does not create enough force to remove many of the beta keratin protein contaminants present in the extracted protein solution. Thus, in some embodiments, high speed centrifugation is employed. Speeds in excess of about 5,000 rpm to about 30,000 rpm can be used. In a specific embodiment, the extracted protein solution is spun at about 20,000 rpm to produce a clarified protein solution of solubilized keratin proteins. In another specific embodiment, the high speed centrifugation step is performed at about 4° C.

A clarified protein solution is produced by the high speed centrifugation of the soluble keratin protein solution.

Dialysis

In many instances during protein purification, dialysis is used to separate or even to concentrate certain protein species present in the sample. Accordingly here, in many embodiments, the clarified protein solution is subjected to a dialysis step to fractionate certain protein species. In some embodiments, a 100 kDa molecular weight cutoff membrane is employed in the purification of alpha-keratose or alpha-kerateine. In other embodiments, a 5 kDa molecular weight cutoff membrane is employed to purify gamma-keratose or gamma kerateine. A common matrix for the dialysis membranes is regenerated cellulose, however, many other membrane preparations suitable for protein purification may be used.

In many instances, pressure is applied to aid in the dialysis process. If the pressure applied is too low, the resultant solutions contain greater protein fragments and peptides. Conversely, if the pressure is too high, the result is protein complex degradation. Thus, in some embodiments, the dialysis is performed under conditions that maintain a transmembrane pressure from about 30 to about 70 psi. In some embodiments the transmembrane pressure is about 30 to about 40 psi, in others it is about 60 to about 70 psi. Further, it is important to minimize the heat buildup developed by the shear stress of pressurized dialysis. Thus, in some embodiments, the dialysis is carried out at a temperature from about 4° C. to about 20° C. In a specific embodiment, the dialysis is carried out at about 15° C.

Additionally, as the solution is dialyzed, the conductivity is adjusted. In some embodiments, the conductivity is adjusted down to about or below 0.6 mS. In some instances, the conductivity is adjusted with water.

Lyophilization

Storage of proteins for any length of time can pose stability problems. Since proteins are generally more stable at colder temperatures, maintenance at low temperatures even for short duration is recommended. Typically, proteins can be freeze-dried (lyophilized) to achieve storage conditions while maintaining protein stability.

In some embodiments, lyophilization is used to produce a protein cake of purified protein. The lyophilization is used to stabilize the extracted keratin proteins. Methods known in the art such as shell freezing followed by vacuum or bulk freezing and applying high heat tend to degrade proteins. Accordingly, in some embodiments, a keratin protein cake, comprising keratose alpha or gamma and/or kerateine alpha or gamma is produced by a lyophilization of a clarified keratin protein solution, optionally after dialysis.

In some embodiments, the clarified protein solution postdialysis is bulk frozen at about −40° C., and then a vacuum is applied until the containment containing the solution reaches about 250 torr. In some embodiments, heat is then applied in a step-wise fashion, bringing the material to about 0° C., then to about 25° C., then to about 37° C., while maintaining 250 torr pressure. In some embodiments, the lyophilization process occurs over a 24 hour period.

Grinding

Precise grinding of the lyophilized material aids in the homogeneity of reconstitution and protein stability. Previous methods involve crude grinding methods, including grinding or chopping of the material in a laboratory blender. In the present invention, some embodiments employ a commercial grinding apparatus to machine the material to a homogenous particle size. In some embodiments, a pharmaceutical mill is employed. In other embodiments, the particle size is about 1000 microns or less in diameter.

It is also important to remove the static charge from the ground material to make it easier to work with. Accordingly, in some embodiments, the ground material has been deionized.

Hydrogel Preparation

Hydrogels were prepared for analysis by carefully weighing the appropriate keratin lyophilized powder or powders. The powders were diluted in either sterile phosphobuffer saline or sterile water to generate the described percent mass to volume ratio. Halofuginone was added at appropriate volumes to achieve the final concentrations desired.

In some embodiments, the hydrogel comprises less than 20% protein in a weight to volume ratio. In other embodiments, the hydrogels comprise less than 19% protein, less than 18%, less than 17%, less than 16%, less than 15%, less than 14%, less than 13%, less than 12%, less than 11%, less than 10%, less than 9%, less than 8%, less than 7%, less than 6%, less than 5%, less than 4% protein, or less than 3% in a weight to volume ratio.

In other embodiments, the hydrogel comprises about 2%, about 3%, about 4%, about 5%, about 6%, about 7%, about 8%, about 9%, about 10%, about 11%, about 12%, about 13%, about 14%, about 15%, about 16%, about 17%, about 18%, or about 19% protein in a weight to volume ratio. In other embodiments, the hydrogel comprises 2%, 3%, 4%, 5%, 6%, 7%, 8%, 9%, 10%, 11%, 12%, 13%, 14%, 15%, 16%, 17%, 18%, or 19% protein in a weight to volume ratio.

In some embodiments, the hydrogel may comprise 80%, 85%, 90%, 95%, 99% or more keratose. The keratose may be alpha-keratose or gamma-keratose, or some combination thereof. In some embodiments, the keratose in the hydrogel comprises 50%, 55%, 60%, 65%, 70%, 75%, 80%, 85%, 90%, 95%, 99% or more alpha-keratose. In other embodiments, the hydrogel comprises 50%, 55%, 60%, 65%, 70%, 75%, 80%, 85%, 90%, 95%, 99% or more gamma-keratose. In alternative embodiments, the hydrogel is substantially free of gamma-keratose. In some embodiments, the hydrogel is substantially free of kerateine. In other embodiments, keratose-based hydrogels are substantially free of disulfide bonds.

In some embodiments, the hydrogel may comprise 80%, 85%, 90%, 95%, 99% or more kerateine. The kerateine may be alpha-kerateine or gamma-kerateine, or some combination thereof. In some embodiments, the kerateine in the hydrogel comprises 50%, 55%, 60%, 65%, 70%, 75%, 80%, 85%, 90%, 95%, 99% or more alpha-kerateine. In other embodiments, the hydrogel comprises 50%, 55%, 60%, 65%, 70%, 75%, 80%, 85%, 90%, 95%, 99% or more gamma-kerateine. In alternative embodiments, the hydrogel is substantially free of gamma-kerateine. In other embodiments, the hydrogel is substantially free of alpha or gamma keratose.

In yet other embodiments, the hydrogels described herein present similar gelation and stability properties of gels of higher percentage protein concentration then have been reported. In some embodiments, compositions of the invention comprise hydrogels of less than 20% protein that exhibit similar gelation and/or stability properties than hydrogels reported in the art that comprise 20% or more protein. In other embodiments, compositions of the invention comprise hydrogels of less than 20% protein that exhibit superior gelation and/or stability properties than hydrogels reported in the art that comprise 20% or more protein.

In other embodiments, methods of the invention comprise making hydrogels of less than 20% protein. Preparing a hydrogel is described above by may comprise the following steps: a) providing keratose, kerateine, or a combination thereof, at a concentration of less than 20% weight to volume in an aqueous medium; b) mixing said keratose, kerateine, or a combination thereof in said aqueous medium; and c) allowing the hydrogel to form. Sometimes, the keratose, kerateine, or a combination thereof has previously been lyophilized. Also, the keratose, kerateine or a combination thereof is provided as a ground protein powder.

Also, the hydrogels described herein do not require additional biomaterials or added crosslinkers to create or maintain structure. Thus, the compositions presented herein are substantially free of added biomaterials or crosslinkers.

Such biomaterials and or crosslinkers include, but are not limited to: albumin, (hydroxyethyl)starch, poly-aspartamide, poly(vinyl alcohol), hyaluronic acid, alginate, chitosan, collagen, gelatin, fibrin, silk, poly(ethylene glycol) (aka PEG), poly(lactic acid) (aka PLA), poly(lactic-co-glycolic acid) (aka PLGA), poly(glycolic acid) (aka PGA), poly (dioxanone), poly(caprolacetone), poly(PCPP-SA anhydride), poly(2-hydroxyethyl methacrylate) (aka pHEMA), dextran, dextran plus glycidylmethacrylate (GMA), cylcodextran, dioleyl phosphatidylethanolamine (DOPE) and other catatonic lipids forming nanoparticles, calcium sulphates (bone powders/pastes), glutaraldehyde, 1-ethyl-3-(3-dimethylaminopropyl)carbodiimide) (aka EDC), methylenebisacrylamide, hexamethylenediisocyanate, 1,4-bis (acryloyl)piperazine, 1,4-cyclohexanedimethanol divinyl ether, 1,4-phenylenediacryloyl chloride, 1,6-hexanediol diacrylate, N-(1-hydroxy-2,2-dimethoxyethyl)acrylamide, di(ethylene glycol) diacrylate, di(ethylene glycol) dimethacrylate, ethylene glycol diacrylate, ethylene glycol dimethacrylate, divinylbenzene, genipin or other common biomaterials or crosslinking agents or agents that are used to bolster structure known in the art. Additional hydrogel forming compositions are described in U.S. Pat. No. 5,854,382.

Halofuginone

In some embodiments, halofuginone is present in the keratin-based hydrogel at a concentration from about 1 µg/ml to about 500 µg/ml. In some particular uses, Halofuginone is present at a concentration of about 22 µg/ml or at about 400 µg/ml. The invention also provides for methods of preparing keratin based hydrogels containing halofuginone. In one embodiment methods of preparing keratin based hydrogels containing halofuginone comprise: A) diluting halofuginone to a desired hydrogel concentration in buffer; B) providing keratose, kerateine, or a combination thereof, in powder form; C) mixing said keratose, kerateine, or a combination thereof in said buffer to attain a concentration of the keratose, kerateine or a combination thereof of less than 20%; and D) allowing the hydrogel to form.

Exemplary Compositions

In particular uses, compositions of the invention comprise a keratin-based hydrogel comprising 95% alpha keratose and 5% gamma keratose and halofuginone at a concentration of about 22 µg/ml. Other hydrogels may comprise 85% alpha keratose and 15% gamma keratose and halofuginone at a concentration of about 400 µg/ml.

Preparation Considerations

The compositions described herein may be produced by mixing dry powder compositions with aqueous solutions to produce solutions of alpha keratose and/or other keratin(s) solubilized therein. The mixing step can be carried out at any suitable temperature, typically room temperature, and can be carried out by any suitable technique such as stirring, shaking, agitation, sonication, etc. Salts, buffers, excipients, pharmaceutically acceptable carriers, gel-forming agents, disintegrants, coatings, anti-adherents, emulsifiers, detergents, reductants, oxidants, proteins, carbohydrates, or other constituent ingredients that may comprise a dry powder. The alpha keratose and/or other keratin(s) may be suspended in solutions, gels, or provided as dry powders. The compositions may be provided as hydrated gels, films, membranes, etc. or in dehydrated form. Compositions in dehydrated form may be provided with sterile or pyrogen-free water or buffer/electrolyte solutions for rehydrating.

Also described herein are compositions comprising aqueous solutions, emulsions, or dry powders intended to be rehydrated with aqueous compositions or emulsions. Such compositions may contain proteins, carbohydrates, salts, buffers, excipients, pharmaceutically acceptable carriers, stabilizers, gel-forming agents, crowding agents, binders, coatings, solubilizers, emulsifiers, detergents, reductants, oxidants, preservatives, sorbents, polar or nonpolar organic solvents, non-aqueous vehicles including edible oils, and aqueous solvents.

The compositions described herein may be non-pyrogenic or sterile. Keratin solutions may be sterile filtered and processed aseptically, or terminally sterilized using ethylene oxide, e-beam, gamma radiation, or other low temperature methods (i.e., <50° C.).

The compositions described herein may be provided in a precursor solution aseptically packaged in a suitable container. For example, a gel precursor solution can be provided in a glass ampoule ready to use directly or after dilution by the user. A user would break open the ampoule, mix in a compound of interest, and use the solution directly or after dilution.

The compositions described herein may be provided preformed and aseptically packaged in suitable containers, such as a flexible polymeric bags, plastic packaging, bottles, or foil envelopes or may be provided as a kit of sterile or non-pyrogenic dry powder in one container and sterile aqueous solution in a separate container for mixing just prior to use. When provided pre-formed and packaged in a sterile container the composition preferably has a shelf life of at least 4 or 6 months (up to 2 or 3 years or more) at room temperature, prior to substantial loss of viscosity (e.g., more than 10 or 20 percent) and/or structural integrity of the gel or hydrogel.

Also described herein are kits, wherein the compositions described herein are provided in a suitable container (e.g. a plastic or glass bottle, sterile ampoule, etc.), optionally packaged in sterile or non-pyrogenic form. The kit may be contained in a hermetically sealed package also in sterile form. The compositions may be provided as powders, liquids, gels, membranes, dressings, creams, and so forth, and may be provided in different volumes. The composition may be provided in a dehydrated from that can be rehydrated using sterile water or solution provided in the kit. The kit can comprise a delivery means or applicator for administering the composition. In addition the, kit may contain printed instructions for using the kit, including descriptions of the compositions, directions for use of the applicator, and other relevant information.

Methods of Treating Wounds in a Subject in Need Thereof

Also provided herein are methods for wound healing in a subject in need thereof comprising an effective amount of a composition comprising a keratin-based hydrogel comprising halofuginone. Further, "subjects" as used herein refers to any mammal that is in need of treatment of a wound. Examples of subjects include, but are not limited to humans, horses, donkeys, cows, sheep, dogs and cats and any mammal under veterinary care. Various keratin-based hydrogel comprising halofuginone compositions are described herein. In such embodiments, the administration of a keratin-based hydrogel comprising halofuginone may be done by topical, subcutaneous, intradermal, intraperitoneal, intramuscular, intravenous, intracerebral, epidural, or transdermal administration.

In other embodiments, the administration of a keratin-based hydrogel comprising halofuginone composition described herein is site-specific and/or spatially restricted. For example, the composition may be administered at a specific place on a tissue to modulate wound healing.

In further embodiments, the wound may be a surgical wound, or a trauma wound.

6. EXAMPLES

Example 1—Halofuginone Release from Keratin Hydrogels

Keratin was extracted and prepared by an oxidative extraction process as described above Keratin obtained through these methods is referred to as keratose. Reference grade halofuginone (HF) powder was synthesized and obtained from Scynexix, Inc., Durham, N.C. HF was diluted in a 4:1 mixture of water and methanol to a concentration of 2.2 mg/mL, and then diluted to the working concentration of 22 µg/mL in sterile PBS. Twenty-two µg/mL working solution of HF was added to the dry keratose powder to form a 10% weight:volume solution. The mixture was incubated overnight at 37° C. to spontaneously form the hydrogel.

Hydrogels with HF were formed as described above at a volume of 100 µL. One hundred µL PBS was placed on top of the hydrogels and the samples were incubated at 37° C. At 1.5, 3, 6, 12, 24 hrs and then daily through 7 days (n=3 per time point), the 100 µL aliquots of PBS were removed from the samples and stored at −80° C. until further analysis was performed. After collecting PBS at each specified time point, a fresh 100 µL aliquot of PBS was placed over the hydrogel for the next time point collection. Total protein was measured at each time point using the Bio-Rad DC™ Protein Assay as recommended by the manufacturer and compared to a standard curve of keratin. The remaining frozen samples were analyzed for HF concentrations according to a previously described HPLC-electrospray tandem mass spectrometric assay. This assay was modified to inject 10 µL of reconstituted sample and was shown to provide acceptable accuracy (within 12%) and precision (less than 11% coefficient of variation) over a range of 1-1000 ng/mL.

The results of the halofuginone release assay are presented in FIGS. 1 & 2. Panel A depicts the release of halofuginone from keratin based hydrogels over time. Halofuginone was present within the hydrogel at a concentration of 22 µg/mL. The release of the halofuginone into PBS buffer was measured over several days. The buffer concentration of 1.5 µg/mL of drug was constant over days 1-4 and slowly decreased thereafter. The inset shows the release characteristics in the first 24 hours. Panel B depicts halofuginone release and keratin protein release from the hydrogel expressed as a percentage of the original amount of drug/protein present within the hydrogel. Correlation between the halofuginone release and keratin protein release (degradation) is greater than 0.98, n=3 for each data point with SEM. These results demonstrate that a stable, extended, controlled release of halofuginone from the keratin-based hydrogel was achieved. Further, the release of halofuginone from the hydrogel mimicked the degradation of the keratin protein in the hydrogel.

Example 2 Halofuginone Containing Keratin Hydrogels in the Treatment of Proud Flesh Legions in Horses A study was conducted in 3 adult horses with lower limb hypergranulation wounds (known as "proud flesh"). A halofuginone containing keratose hydrogel was prepared as described above to produce a final hydrogel that contained 10% keratose made up of 85% alpha keratose and 15% gamma keratose with a final halofuginone concentration of 400 µg/mL. This composition was applied to the wounds to achieve a daily dose of 30 µg/mL/day. Shown in FIG. 3 are images of wounds on one horse receiving treatment with a halofuginone containing keratin based hydrogel. The scab debrided every other day and the hydrogel was applied to prevent hypergranulation reoccurrence. By day 18-24, the wound is nearly healed, a process that usually takes 90 days using conventional treatment. All three horses showed similar healing rates. These results demonstrate that the treatment of hypergranulation wounds with halofuginone containing keratin based hydrogels is an effective treatment and accelerates the process compared to conventional treatments.

We claim:
1. A composition comprising:
    a. keratose, wherein said composition forms a hydrogel at a keratose concentration of less than 20%, and wherein the keratose in the formed hydrogel is substantially free of disulfide bonds; and
    b. halofuginone, wherein the halofuginone disperses within the formed hydrogel,
    wherein the composition and the hydrogel formed by the composition are substantially free of added biomaterials.
2. The composition of claim 1, wherein said protein concentration is 10% or less.
3. The composition of claim 1, wherein said hydrogel is formed between about 25° C. and about 37° C.
4. The composition of claim 1, wherein said hydrogel is stable at about 25° C. to about 37° C.
5. The composition of claim 1, wherein said hydrogel comprises at least 85% or more alpha-keratose.
6. The composition of claim 1, wherein said hydrogel is substantially free of kerateine.
7. The composition of claim 1, wherein said halofuginone is present at a concentration of about 1 µg/ml to about 500 µg/ml.
8. The composition of claim 1, wherein said halofuginone is released from the hydrogel at a controlled rate.
9. The composition of claim 1, wherein said halofuginone is released from the hydrogel at a similar rate to the breakdown of the hydrogel.
10. The composition of claim 1, wherein said keratose is derived from a human keratin source.
11. The composition of claim 10, wherein said human keratin source is hair.
12. A method of treating a wound comprising applying an effective amount of the composition of claim 1 to a wound.
13. The method of claim 12, wherein the composition is topically applied.
14. The method of claim 12, wherein the application is site-specific and spatially restricted.
15. The method of claim 12, wherein said wound is selected from the group consisting of: a burn wound, surgical wound, or trauma wound.
16. A kit for administering an alpha keratose composition to a recipient in need thereof comprising:
    a. at least one container comprising individual premeasured dosages, the containers including the composition from claim 1;
    b. optionally, solutions for rehydrating dehydrated compositions;
    c. a means for administering an alpha keratose composition to a recipient in need thereof; and d. instructions describing a method for administering the composition to a subject in need thereof.

* * * * *